United States Patent [19]

Mulholland

[11] Patent Number: 5,520,669

[45] Date of Patent: May 28, 1996

[54] INTRA-RECTAL DRAIN AND RECEPTACLE FOR FECAL INCONTINENCE

[76] Inventor: Kevin J. Mulholland, 1162 Texas Hill Rd., Huntington, Vt. 05462

[21] Appl. No.: 276,354

[22] Filed: Jul. 19, 1994

[51] Int. Cl.⁶ .................................................. A61F 5/44
[52] U.S. Cl. .......................................... 604/328; 604/348
[58] Field of Search .................................. 604/348, 355, 604/327–331, 337; 600/29–31; 606/197

[56] References Cited

U.S. PATENT DOCUMENTS

| | | | |
|---|---|---|---|
| 3,918,452 | 11/1975 | Cornfeld | 604/286 |
| 3,938,521 | 2/1976 | Ritota et al. | 604/328 |
| 3,964,111 | 6/1976 | Packer | 604/355 |
| 4,030,500 | 6/1977 | Ronnquist | 604/328 |
| 4,182,332 | 1/1980 | Delaney | 604/328 |
| 4,739,767 | 4/1988 | Lahr | 606/197 |
| 5,217,439 | 6/1993 | McClusky | 604/275 |
| 5,261,898 | 11/1993 | Polin et al. | 604/328 |

Primary Examiner—Randall L. Green
Assistant Examiner—Mark O. Polutta
Attorney, Agent, or Firm—Donald W. Meeker

[57] ABSTRACT

A spring is imbedded in a collapsible rubberized ring with a flat broad bottom and peaked top having a wide inwardly sloping top face. The ring compresses together in a linear shape for anal insertion and expands out into a ring inside past the interior anal sphincter. A tapering funnel-shaped resilient neck connects the ring to an external receptacle to collect excretions. The receptacle may be formed integrally with the neck and ring or may be detachable. A gas release valve is built into the top of the receptacle. An enema tube may be inserted in the neck. Reinforcement on two opposing sides of the ring facilitates collapse of the ring by pulling on the neck for easy removal of the device from the patient. The spring may be a coil spring, a flat spring or a combination of the two. A slotted tube with a plunger and handle may be used to insert the compressed ring into the anal opening of a patient. The ring, neck, and receptacle are formed of a non-allergenic polymer such as Latex (TM).

12 Claims, 2 Drawing Sheets

INTRA-RECTAL DRAIN AND RECEPTACLE FOR FECAL INCONTINENCE

DESCRIPTION

BACKGROUND OF THE INVENTION

1. Technical Field

The present invention relates to a medical device related to fecal incontinence and in particular to a fecal collection receptacle connected by a flexible tube to an insertable broad low pressure intra-rectal ring.

2. Description of the Prior Art

Fetal incontinence is a medical problem which causes much discomfort, embarrassment, and loss of self-esteem for patients and causes irritation and considerable work for healthcare staff. Elderly patients are especially prone to this problem, with sometimes over half of geriatric patients in care facilities having occasional fetal incontinence problems and often over ten percent having persistent fetal incontinence problems.

Causes for fetal incontinence vary from treatable situations of fecal incontinence caused by fetal stasis and some physical diseases such as carcinoma of the rectum and colon and ischemic colitis or diverticular disease, to untreatable fecal incontinence caused by neurologic disorders such as dementia, and physical diseases such as megacolon, Crohn's disease, and rectal prolapse. Drugs such as analgesics and hematinics and excessive use of purgatives can also cause fecal incontinence.

In untreatable cases, trying to contain the fecal matter as it is excreted seems to be the primary goal to save embarrassment and considerable mess. Diapers are not the best solution since there is still a considerable mess and cleanup care associated with the contained mess in the diapers, as well as occasional leakage problems out of the diapers. All external fecal collection means have a similar problem of still having a contained localized mess and periodic leakage.

Other fetal incontinence devices which are inserted in the rectum tend to be harsh on tissues and cause irritation and potential infection problems. Prolonged use of such devices is generally not possible due to the damage caused by the devices themselves.

Disclosure of Invention

The present invention provides, on a fetal collection receptacle and tapered neck, a broad-lipped ring for intra-rectal insertion, which broad-lipped ring creates only a low pressure on the rectal mucosal tissues, which is less than the mean arterial pressure of approximately 100 mm Hg. This would not cut off the blood supply and would avoid ulcerated tissue. A flat broad base of the broad-lipped ring would lie flat against the tissue creating a tight seal to prevent leakage, while a long sloping inner top of the broad-lipped ring would funnel material into the chute and fecal collection bag.

A coiled or flat spring within the broad-lipped ring would enable the ring to be compressed into a flat linear shape for ease of insertion of the ring into the anus of the patient. Once inserted past the anal sphincter, the spring would then unfurl to open the ring to its normal circular shape and cause the ring to lie open with the flat broad base of the ring pressing flat against the interior of the pelvic diaphragm surrounding the opening above the internal anal sphincter. This occludes the external anal sphincter and allows feces to flow from the rectum through the circular ring, passing through the cone-shaped tapered neck into an external receptacle. External fecal soiling would be circumvented and the waste matter would be confined within the system, never contacting the skin of the patient or any external clothing or bedcovers.

A piston moved by a handle through a slotted cylinder could facilitate insertion of the ring in its compressed flat linear shape requiring less contacting of the skin of the patient and could provide improved user friendliness.

The flexible tapered neck extending downwardly from the ring into the external flexible receptacle enables the receptacle to be positioned as desired to enable a patient to walk around by strapping the receptacle to the leg of the patient or otherwise affixing. The receptacle may be fabricated of a variety of materials in a variety of shapes to suit the needs of the patient. Along the top of the receptacle a gas release valve prevents the receptacle from filling with gas and thereby avoids stretching or breakage of the receptacle.

Inserting a tube into the tapered neck of the invention presents a closed system for giving enemas with a built-in receptacle and closed system to contain all of the liquid and fetal matter with no possibility of creating a mess.

Reinforcing two or more opposite sides of the ring and leaving the other two or more opposing sides without reinforcement creates a ring that would automatically be pulled into a linear shape by tugging on the neck of the invention enabling the device to be removed easily from the patient by simply tugging on the neck of the invention causing the ring to collapse into a linear shape and slip easily out of the rectum of the patient.

Constructing the invention of Latex (TM) or other non-allergenic pliable material creates a relatively inexpensive, but very effective fecal collection device which may be removed and disposed of, requiring no contact with the fecal matter. The ease of insertion of the device makes replacement of a full soiled fecal collector with an empty clean fecal collector no problem.

BRIEF DESCRIPTION OF THE DRAWINGS

These and other details and advantages of my invention will be described in connection with the accompanying drawings, which are furnished only by way of illustration and not in limitation of the invention, and in which drawings.

BEST MODE FOR CARRYING OUT THE INVENTION

Figure 10:
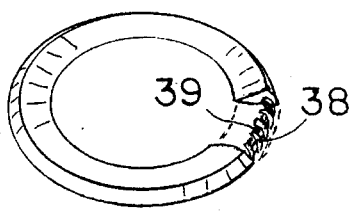
FIG. 10 is a perspective view in partial section showing an alternate embodiment of the invention with a combined flat spring and coiled spring.

In FIGS. 1, 2, 3, and 5 an intra-rectal drain and receptacle for fecal incontinence 20 comprises a collapsible rubberlike springy circular ring 22 having a broad flat bottom surface 40 (in FIG. 5) and a wide inwardly sloping upper surface 24. The ring 22 may be squeezed closed as in FIG. 2 for insertion into the anus of the patient and allowed to spring open inside the patient as in FIG. 3. Extending downwardly from the ring a resilient water-tight collapsible neck 28 tapers downwardly in a funnel shape from the ring. Flexibly connected with a water-tight connection to the neck, a resilient water-tight receptacle 30 receives and stores the waste matter for disposal. A gas rlease valve 29 is built into the receptacle 30 adjacent to the top of the receptacle. The gas release valve could be a double rubber flap arrangement or any type of valve allowing a one way outward release of gas and not liquid. The broad flat bottom of the ring 22 presses gently (less than mean arterial pressure) against the tissue above the internal anal sphicter to create a positive seal against leakage. The inwardly sloping top surface 24 of the ring directs waste into the opening 23 and down the funnel-like resilient neck 28 into the receptacle In FIG. 5, the ring 22 is substantially triangular in cross-section with the widest side on the bottom 40 and two unequal sides on the top 24 and B6 forming a peak 26 with the wider top side 24 on the interior of the circular ring sloping inwardly toward the center of the circular ring. Inside the ring under the peak 26, a spring 26 is imbedded in the ring 22. The spring may be a soil spring 38 as in FIGS. 5 and 7, a flat spring 39 as in FIG. 8, or a flat spring a 39 and a coiled spring 38 combined together as in FIG. 10.

Figure 4:
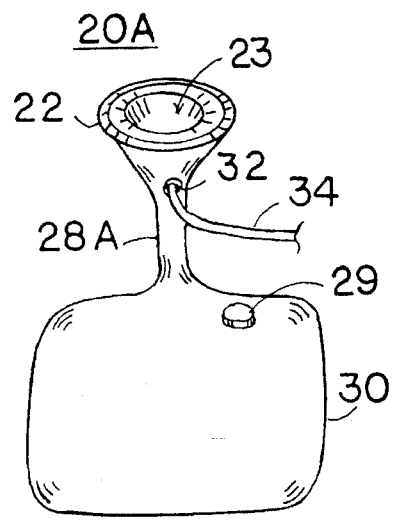
FIG. 4 is a perspective view of an alternate embodiment of the invention having an enema tube inserted into the neck of the invention.
Figure 5:
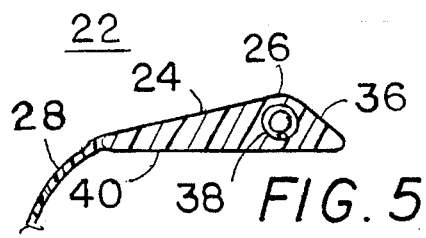
FIG. 5 is an exploded cross-sectional view of the ring of the invention taken through 5—5 of FIG. 1 showing the spring imbedded in the ring.

In FIG. 4 an enema tube 34 may be inserted in the tapering neck in a water-tight connection 32, and enema solution may be pumped through the tube 34 into the neck 28 and on into the bowel of the patient. With this enclosed system there is no mess created in the process of giving the enema.

Figure 1:
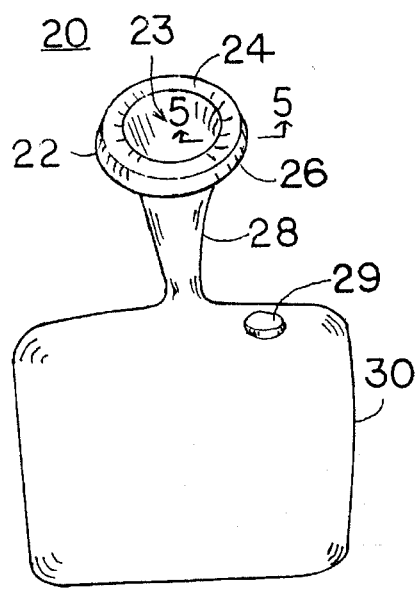
FIG. 1 is a perspective view of the preferred embodiment of the invention with the ring open under the force of the coiled spring.
Figure 2:
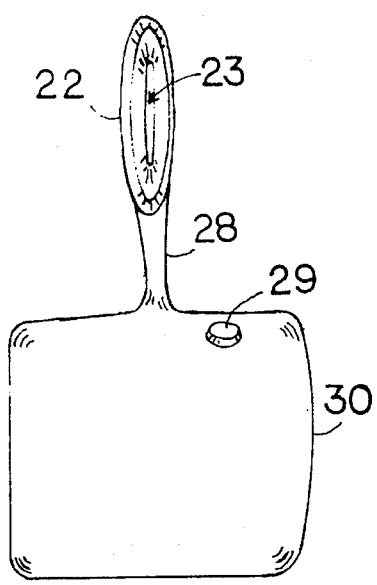
FIG. 2 is a perspective view of the invention with the ring closed for insertion in a patient.
Figure 3:
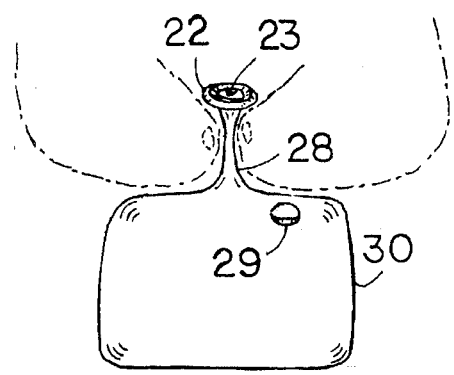
FIG. 3 is a perspective view showing the invention installed in the body of a patient.
Figure 11:
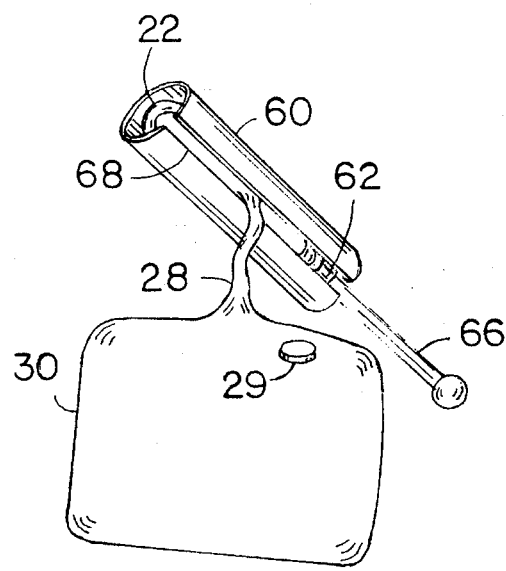
FIG. 11 is a perspective view showing an insertion tube used to install the invention in a patient.

The ring 22 may be squeezed together as in FIG. 2 and inserted by hand or, as in FIG. 11, insertion may be accomplished by using a tube 60 having a longitudinal slot 68 and a plunger 62 with a handle 66 at one end of the tube. The ring 22 is squeezed together into a linear shape, inserted in the tube 60 with the neck 28 protruding out through the slot 68, and the handle 66 pushed causing the plunger to insert the ring 22 into the rectal opening of a patient.

Figure 6:
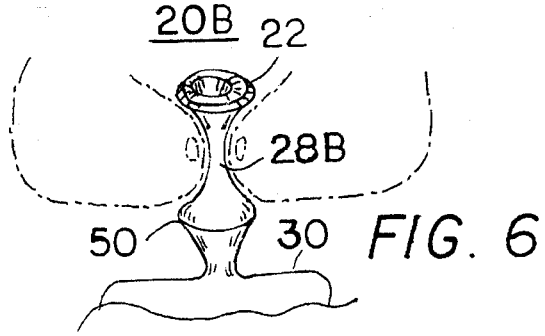
FIG. 6 is a perspective view of an alternate embodiment of the invention with a second ring outside the patient.

In FIG. 6 an alternate embodiment of the invention 20B shows a second ring 50 around the neck 28 spaced apart from the first ring 22 so that when the first ring 22 is inserted into an anus (shown dashed) of a patient with the first ring 22 opening past an interior anal sphincter of the patient, the second ring 50 will remain Just outside the anus so that the two rings hold the invention in place to prevent slippage of the invention in or out.

Figure 9:
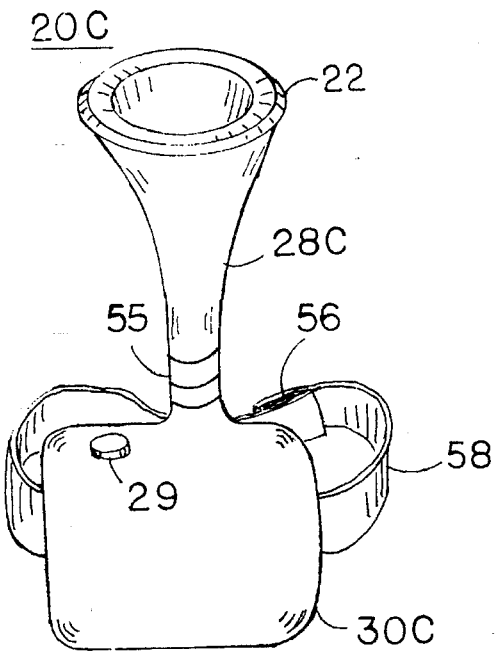
FIG. 9 is a perspective view of an alternate embodiment of the invention having a removable receptacle attached to the neck of the invention.

The ring 22 and neck 28 and receptacle 30 may be fabricated in one piece by molding a flexible non-allergenic polymer such as Latex (TM). This is primarily intended as a disposable item. Alternately, as in FIG. 9, the receptacle 30C is removably attached by a water-tight connection 55to the neck 28C. The receptacle may be fitted with a leg strap 58 adjustably attached by Velcro (TM) fasteners 56 or other means to a leg of a patient for greater mobility. The receptacle 30 may be shaped to suit any desired usage by a patient.

Figure 7:
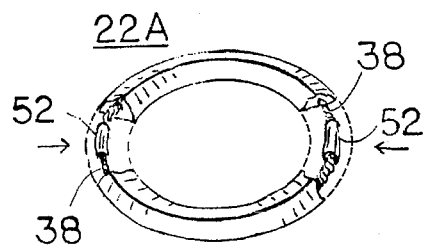
FIG. 7 is a perspective view in partial section showing an alternate embodiment of the ring with two opposing sides of the ring reinforced.
Figure 8:
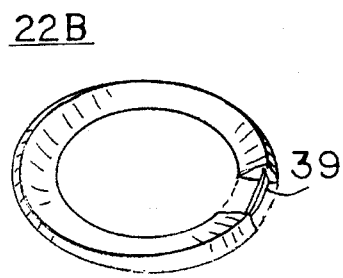
FIG. 8 is a perspective view in partial section showing an alternate embodiment of the invention with a flat spring.

In FIG. 7, the ring 22A is reinforced on two opposing sides of the ring with a restricting band 52 around a portion of the spring 38, so that pulling on the neck of the ring, when the ring is in place i5 inside a patient, will cause two non-reinforced sides of the ring to collapse inwardly pulling the ring into a linear shape allowing the ring to slip easily out of the patient.

It is understood that the preceding description is given merely by way of illustration and not in limitation of the invention and that various modifications may be made thereto without departing from the spirit of the invention as claimed.

I claim:

1. An intra-rectal drain and receptacle for fecal incontinence comprising:

a rubberlike collapsible springy circular ring having a broad flat bottom surface and a wide inwardly sloping upper surface, wherein the ring may be squeezed closed and allowed to spring open;

extending downwardly from the ring a resilient water-tight collapsible neck tapering downwardly in a funnel shape from the ring;

flexibly connected with a water-tight connection to the neck, a resilient water-tight receptacle, wherein the receptacle is provided with a gas release valve;

wherein the ring is substantially triangular in cross-section with the widest side on the bottom and two unequal sides on the top forming a peak with the wider top side on the interior of the circular ring sloping inwardly toward the center of the circular ring;

inside the ring under the peak, a circular spring imbedded in the ring;

wherein the ring is reinforced on opposing sides of the ring, so that pulling on the neck of the ring, when the ring is in place inside a patient will cause non-reinforced sides of the ring to collapse inwardly pulling the ring into a linear shape allowing the ring to slip out of the patient.

2. The invention of claim 1 further comprising inside the ring under the peak, a circular spring imbedded in the ring.

3. The invention of claim 1 wherein the spring is a coil spring.

4. The invention of claim 1 wherein the spring is a flat spring.

5. The invention of claim 1 wherein the spring is a flat spring and a coiled spring combined together.

6. The invention of claim 1 further comprising a tube inserted in the tapering neck in a water-tight connection, wherein enema solution may be pumped through the tube into the neck.

7. The invention of claim 1 further comprising a tube having a longitudinal slot and a plunger with a handle at one end of the tube, wherein the ring may be squeezed together into a linear shape, inserted in the tube with the neck protruding out through the slot, and the handle pushed causing the plunger to insert the ring into the rectal opening of a patient, after which the tube is removed.

8. The invention of claim 1 further comprising a second ring around the neck spaced apart from the first ring so that when the first ring is inserted into an anus of a patient with the first ring opening past an interior anal sphinctor of the patient, the second ring will remain Just outside the anus so that the two rings hold the invention in place.

9. The invention of claim 1 wherein the ring and neck and receptacle are fabricated in one piece by molding a flexible non-allergenic polymer.

10. The invention of claim 9 wherein the polymer is a disposable elastomer such as LATEX (TM).

11. The invention of claim 1 wherein the receptacle is removably attached by a water-tight connection to the neck.

12. The invention of claim 11 wherein the receptacle is shaped to suit any desired usage by a patient.

* * * * *